United States Patent
Molgaard-Nielsen (10) Patent No.: US 8,235,946 B2
(45) Date of Patent: Aug. 7, 2012

(54) HAEMOSTATIC VALVE

(75) Inventor: Arne Molgaard-Nielsen, Copenhagen (DK)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/290,401

(22) Filed: Oct. 30, 2008

(65) Prior Publication Data
US 2009/0125103 A1  May 14, 2009

Related U.S. Application Data

(60) Provisional application No. 61/001,019, filed on Oct. 30, 2007.

(51) Int. Cl.
*A61M 5/178* (2006.01)
(52) U.S. Cl. ............. 604/167.04; 604/167.01; 604/246; 604/247; 604/249; 604/256; 604/264
(58) Field of Classification Search .......... 604/246–249, 604/256, 164.01, 264, 167.04, 167.01
See application file for complete search history.

(56) References Cited

U.S. PATENT DOCUMENTS

| | | | |
|---|---|---|---|
| 4,222,126 A * | 9/1980 | Boretos et al. | 623/2.19 |
| 4,540,411 A * | 9/1985 | Bodicky | 604/167.05 |
| 4,673,393 A | 6/1987 | Suzuki et al. | |
| 5,104,389 A * | 4/1992 | Deem et al. | 604/264 |
| 5,143,463 A * | 9/1992 | Pozil et al. | 401/6 |
| 5,176,652 A | 1/1993 | Littrell | |
| 5,330,437 A * | 7/1994 | Durman | 604/167.04 |
| 5,334,164 A * | 8/1994 | Guy et al. | 604/248 |
| 5,350,364 A * | 9/1994 | Stephens et al. | 604/167.06 |
| 5,484,418 A * | 1/1996 | Quiachon et al. | 604/167.03 |
| 5,643,227 A | 7/1997 | Stevens | |
| 5,865,807 A * | 2/1999 | Blake, III | 604/167.06 |
| 5,913,847 A * | 6/1999 | Yoon | 604/523 |
| 6,024,729 A | 2/2000 | Dehdashtian et al. | |
| 6,083,203 A * | 7/2000 | Yoon | 604/167.01 |
| 6,283,994 B1 * | 9/2001 | Moe et al. | 623/2.12 |
| 6,981,996 B2 | 1/2006 | Shaner et al. | |
| 2004/0178586 A1 | 9/2004 | Junge | |

(Continued)

FOREIGN PATENT DOCUMENTS

EP  0538060  4/1993

(Continued)

OTHER PUBLICATIONS

PCT/US08/012285, Mar. 3, 2009, William Cook Europe ApS Int'l Search Report.

(Continued)

*Primary Examiner* — Bhisma Mehta
*Assistant Examiner* — Edelmira Bosques
(74) *Attorney, Agent, or Firm* — Richard J. Godlewski (57) ABSTRACT

There is disclosed a tri-leaflet valve (100) in which the leaflets (102) extend for substantially the entire length of the valve (100). The valve (100) is provide with a waist (106). An element (16) inserted in the tri-leaflet valve (100) can be sealed by closure of the valve (100), for example by pressurization or twisting. The seat is more effective then prior art seals.

18 Claims, 5 Drawing Sheets

U.S. PATENT DOCUMENTS

| | | | |
|---|---|---|---|
| 2005/0113757 A1* | 5/2005 | McFarlane | 604/167.03 |
| 2005/0171479 A1 | 8/2005 | Hruska et al. | |
| 2006/0025854 A1* | 2/2006 | Lashinski et al. | 623/1.25 |
| 2006/0071432 A1* | 4/2006 | Staudner | 277/630 |

FOREIGN PATENT DOCUMENTS

| | | |
|---|---|---|
| EP | 0550069 | 7/1993 |
| WO | 9211880 | 7/1992 |
| WO | 9945983 | 9/1999 |
| WO | 2006061356 | 6/2006 |

OTHER PUBLICATIONS

PCT/US08/012285, Mar. 3, 2009, William Cook Europe ApS Written Opinion.

* cited by examiner

HAEMOSTATIC VALVE

CROSS-REFERENCE TO RELATED APPLICATIONS

This application claims priority of provisional application Ser. No. 61/001,019, filed Oct. 30, 2007.

TECHNICAL FIELD

The present invention relates to a haemostatic valve for use, for example, in an introducer or deployment device of the type employed for delivering and deploying stents, stent grafts, vena cava filters, occlusion devices and other implants and prostheses into a lumen or organ of a patient. The introducer or deployment device can also be of a type used for diagnosis as well as for the carrying out of medical procedures and treatments.

BACKGROUND OF THE INVENTION

Examples of such valves can be found, for instance, in U.S. Pat. No. 4,673,393, U.S. Pat. No. 5,176,652 and US-A-2005/017,479.

A difficulty arises with the use of such a series of seals, however, in that in order to have good sealing characteristics they also tend to create a significant resistance to movement of an insert therein, which can substantially impair the operability of the insert by making it too hard to slide within the sheath. This can in some instances lead to damage of the insert, for example by kinking. This risk is particularly acute for inserts which are by necessity very flexible or of a small diameter.

In order to mitigate the above disadvantages, it is also known to use a haemostatic valve which can be opened and closed under the clinician's control. This has the advantage that an element can be inserted into the sheath and moved therealong with relative ease while the controllable haemostatic valve is in an open configuration. Once the insert is in place the valve can be tightened to seal. Such tightening is also advantageous during the procedure of insertion of the device into the sheath assembly. In practice, it is often necessary for such a solution also to include a valve which self-seals, such as one or more of the disk-shaped valves mentioned above to secure sealing during handling.

Such selectively openable and closable valve elements typically have an elongate valve member of tubular form which can be closed by twisting or by application of pressure laterally on the valve element by means of one or more movable closing plates.

U.S. Pat. No. 4,673,393, U.S. Pat. No. 5,176,652 and U.S. Pat. No. 6,981,996 disclose valve assemblies which include substantially planar valve elements of disc-shape with a number of slits therein. An insert, such as a pusher, dilator or other elongate element, can pass through the slit or slits and into the sheath of the deployment of the device. When such inserts are removed, the slits close in order to close the valve element.

There are a number of compromises with such valve elements. When an insert is passed through the valve to open the slits, the seal is no longer fluid tight, with the result that there can be leakage through the valve element. This problem can be mitigated by designing a valve element with an increased closure pressure, whereby the edges of the slit or slits push tightly against the insert so as to close around this to reduce leakage paths. However, increasing closure pressure increases the effective friction between any item inserted within the valve and the valve itself, which can make it harder to slide any insert through the valve. Such additional friction can also cause damage to any insert held therewithin and potentially cause damage to the valve itself. It will be appreciated that if such damage occurs in the middle of a medical procedure this can be highly disadvantageous, at worst resulting in an abortive procedure.

As explained above, attempts have been made to try to resolve the problem with such valves by providing a plurality of valves in series, with the slit or slits of each valve element being rotated relative to one another so as to provide a more effective seal. However, even though this might improve the sealing characteristics of the valve, it does not satisfactorily deal with the problem of increased pressure on or friction against the insert held therewithin.

US-A-2005/0,171,479 discloses a different type of valve element which is formed of an elongate tubular member which can be twisted so as to fold into a closed position at its centre. The material forming the valve element is sufficiently flexible that it can wrap itself around an insert held within the valve, thereby to provide the required seal. This type of valve has the advantage that when the valve element is opened, that is when it is in an untwisted state, it provides no or substantially no friction on an insert held therewithin. Of course, in practice it is necessary to provide additional sealing/valve elements. It is, for example, known to add disc-shaped seals of the type described above. In US-2005/0171479, for example, there are provided three disc-shaped seals in addition to the twistable cylindrical seal.

Another twistable seal is disclosed in US-2004/078586

An additional problem with the twistable seals disclosed in US-2005/0171479 and US-2004/0178586 is that the sealing efficiency of these seals is determined by the depth of the seal in the longitudinal direction of the valve, in practice the depth of the seal which comes into contact with the outer walls of the insert. This can be seen for example in FIG. 24 of US-A-2005/0171479 and in FIG. 2 of US-A-2004/0178586, in which only a small portion of the twistable valve element contacts the insert, thus providing a relatively narrow seal. A narrower seal provides less sealing effect and often also requires the provision of additional seals, such as the disc-shaped seals used in the device of US-A-2005/0171479.

Therefore, these twistable seal elements do not mitigate all of the disadvantages of haemostatic seals.

Figure 1:
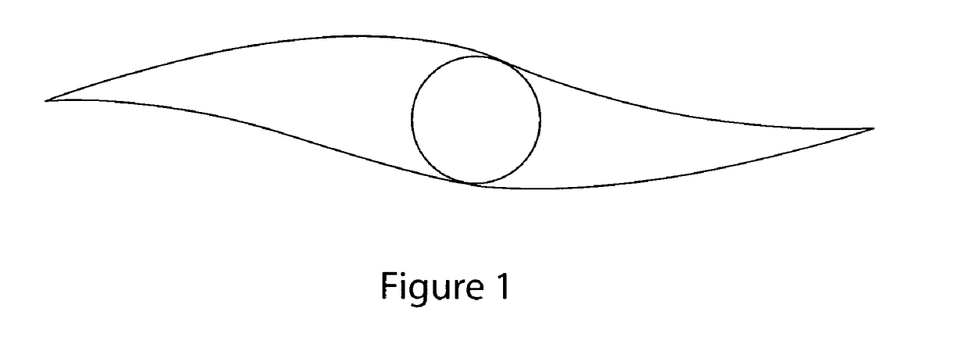
FIG. 1 shows in schematic form a cross-sectional plan view of an example of prior art two-leaflet valve.

Another valve element for use in such deployment devices and also for endoluminal medical procedures includes a flexible valve element provided with two facing leaflets which are able to contact one another when the valve is closed so as to provide a seal. Particularly, one end of the valve element keeps the leaflets open, for example by provision of a support element holding to the two leaflets apart. At the other, free end, the leaflets can be made to contact one another when the valve is in a closed configuration, for example by sealing the side edges of the leaflets together. FIG. 1 shows a cross sectional view of an example of such a two-leaflet valve, in which an insert is located within the valve, causing the two leaflets to open.

A problem with this type of valve, as can be seen in FIG. 1, is that the valve element is unable to close well around the insert, leaving large apertures allowing leakage of fluid through the valve leaflets.

SUMMARY OF THE INVENTION

The present invention seeks to provide an improved valve, in particular a haemostatic valve.

The present invention also seeks to provide an improved introducer or deployment device.

According to an aspect of the present invention, there is provided a valve element formed of at least three elongate flexible leaflets arranged so as to provide a polygonal passage therebetween when the valve element is in an open configuration, the leaflets being able to close in on one another along at least a portion thereof, thereby to provide a seal.

Advantageously, the leaflets are sealed to one another along adjacent longitudinal sides thereof. It is envisaged that the leaflets could be sealed to one another by bonding, welding or during fabrication of the valve. For example, the valve could be formed as a unitary structure, for example by extrusion, vacuum or flow moulding.

In the preferred embodiment, there are provided three leaflets.

Advantageously, the leaflets extend along a major portion of the length of the valve. Most preferably, the leaflets extend for substantially the entire length of the valve.

In the preferred embodiment, the valve has a waisted or hourglass configuration.

The valve may be formed of a compliant or non-compliant material. The valve may be made of polyurethane, silicon, polychloroprene (Neoprene), styrene Butadiene, styrene ethylene Butadiene, latex, a rubber or rubber-like material.

In another embodiment, the valve is made of a non-compliant material, for example polyethylene terephthalate (PET), polyethylene, nylon, a plastics is material, or any other relatively non-compliant material known in the art.

The valve may be provided with a hydrophilic coating, which has the advantage of reducing function and of filling any sealing gaps.

According to another aspect of the present invention, there is provided a medical treatment device, an introducer or deployment device including a valve element as specified herein.

According to another aspect of the present invention, there is provided a valve assembly including a valve element as herein specified and means for configuring the valve element into a closed configuration.

Preferably, the configuring means includes a pressurizable chamber within which the valve element is located, pressurization of the chamber causing the valve leaflets to close onto one another, thereby to seal the valve.

In another embodiment, the configuring means includes a twisting element operable to twist and thereby to close the valve.

According to another aspect of the present invention, there is provided a valve element formed of at least two leaflets arranged so as to provide a passage therebetween when the valve element is in an open configuration, the leaflets being able to close in on one another along at least a portion thereof, thereby to provide a seal; wherein the valve element is formed of a substantially non-compliant material.

DESCRIPTION OF THE DRAWINGS

Embodiments of the present invention are described below, by way of example only, with reference to the accompanying drawings, in which.

DESCRIPTION OF THE PREFERRED EMBODIMENTS

Figure 2:
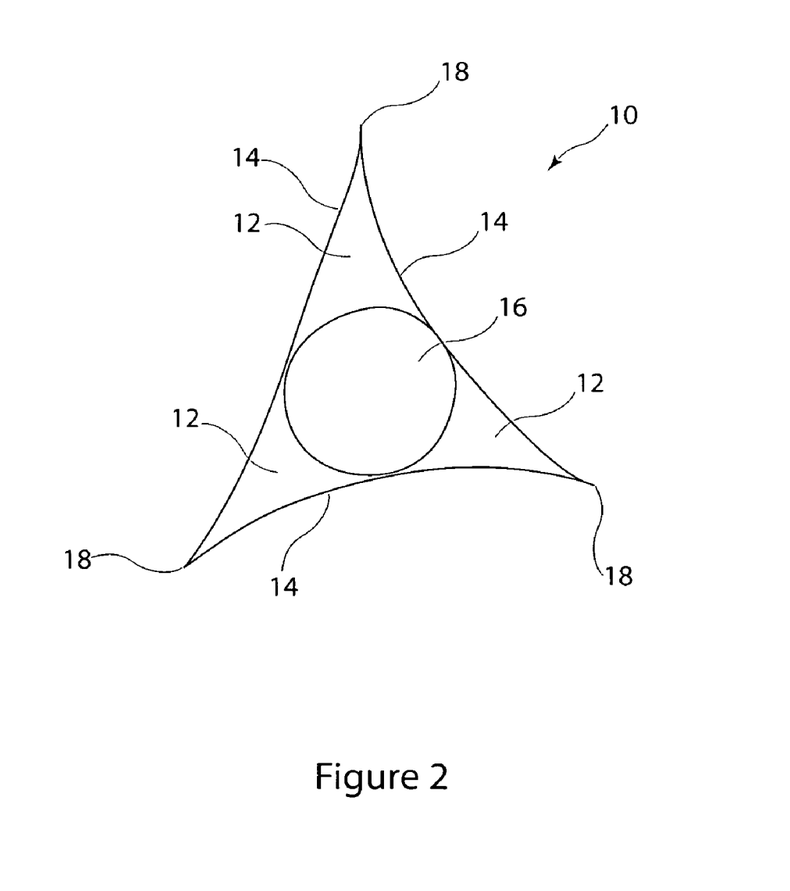
FIG. 2 is a schematic view of an embodiment of tri-leaflet valve, shown in cross-section.

Referring to FIG. 2, this shows in schematic form a cross-sectional view of an embodiment of tri-leaflet valve 10, taken substantially perpendicularly to the longitudinal direction of the valve element 10 and at a centre portion of the valve element. The valve 10 is shown in an unbiased condition, that is without being pressed or otherwise biased to force the material forming valve leaflets 14 to seal onto an insert 16.

Before explaining in detail the features of the valve 10, it is useful to point out some of its main characteristics. A comparison of FIGS. 1 and 2 will show that the example of tri-leaflet valve 10 shown in FIG. 2 provides gaps 12 between the leaflets 14 and the insert 16 which in total area are much smaller than the gaps existing with a two-leaflet valve. Moreover, in light of the fact that two adjacent leaflets 14 of a tri-leaflet valve 10 are required to cover a smaller arc or radial area of the insert 16 held within the valve, the leaflets 14 can seal better than in the case of a two-leaflet valve where the two adjacent leaflets Must, at either side, cover 50% of the insert held therewithin.

It is not ruled out that the valve 10 could have more than three leaflets, such as 4, 5 or 6. However, increasing the number of leaflets in the valve increases the amount of material of the leaflets of the valve 10 which contacts the insert 16 even when the valve 10 is in a not fully sealing or open condition as shown in FIG. 2. This can increase the friction between the valve 10 and the insert 16 during periods in which it is desired to slide the insert into and out of the valve 10. In this regard, it has been found that a tri-leaflet valve provides the best combination of characteristics of sealing and low friction and is thus the preferred option.

Figure 3:
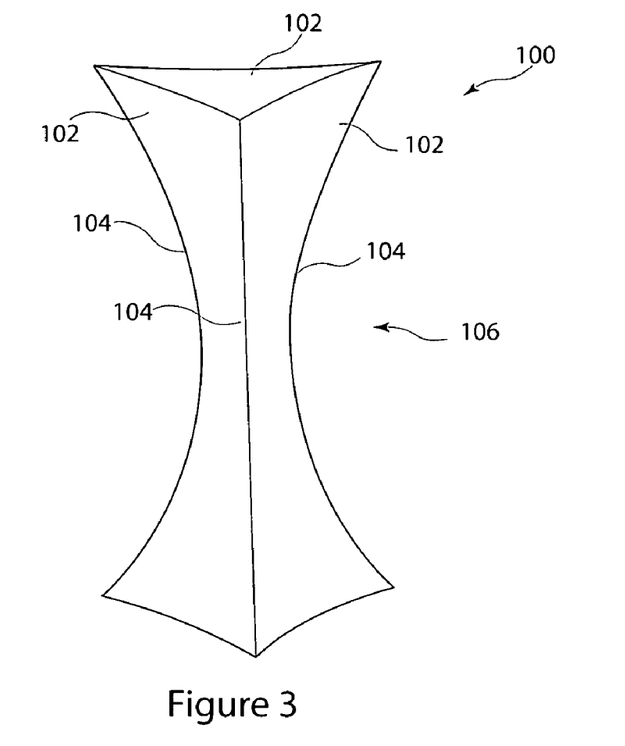
FIG. 3 is a front elevational view of a preferred embodiment of tri-leaflet valve.
Figure 4:
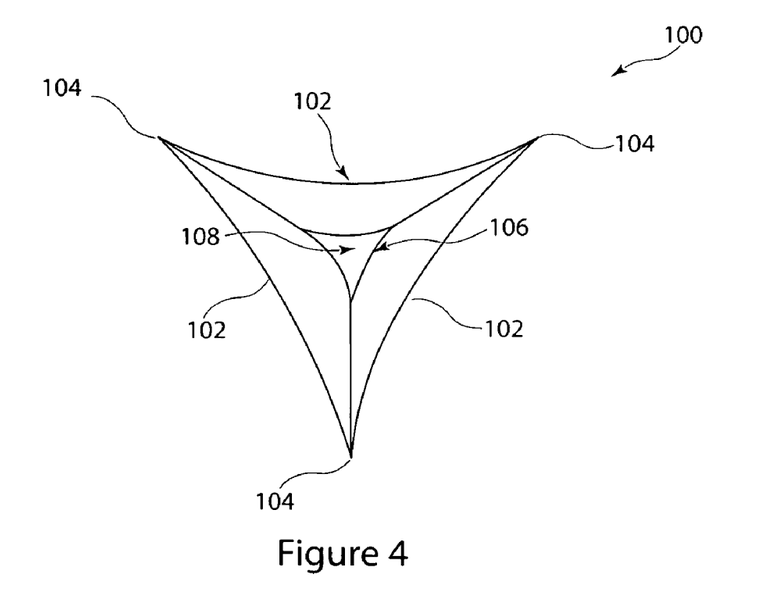
FIG. 4 is a plan view of the valve of FIG. 3.

The shape of the valve 10 can take a variety of forms, the preferred of which is shown in FIGS. 3 and 4 and described in further detail below. In one embodiment, the three leaflets 14 are substantially rectangular along their lengths such that the valve element 10 is substantially cylindrical throughout its length. It may be triangular in axial cross-section but is preferably formed such that each leaflet 14 tends naturally to curve inwardly towards the centre of the valve element 10, shown in FIG. 2. This curvature of the leaflets 14 can be achieved by stretching the apices 18 at the junctions between two adjacent leaflets 14, in a direction away from the central axis of the valve 10. In an alternative, the valve 10 can be formed to have this shape when in a relaxed condition.

The material forming the leaflets 14 could be any suitable material, the preferred being polyurethane, silicon, polychloroprene (Neoprene), styrene Butadiene, styrene ethylene Butadiene, latex, a rubber or rubber-like material. The leaflets 14 can be formed as a single layer of material but in some instances could be multilayered.

It is preferred that the internal surfaces of the leaflets 14 are provided with a hydrophilic coating of a suitable type. This has the advantage of reducing friction between the valve leaflets 14 and an insert 16 and can also, as a result of the conformability of such hydrophilic coatings, assist in filling in any gaps 12 between the valve 10 and the insert 16 so as to optimize the sealing effect.

As will be apparent in FIG. 2, for example, it is preferred that the valve 10 has a minimum open diameter which substantially contacts an insert 16 intended to be held therewithin. This is not, however, a requirement of the valve 10 as this could also work more than satisfactorily with inserts of smaller diameter than the insert 16, as well as inserts larger than the insert 16 shown in FIG. 2, in which case the leaflets 12 would be biased outwardly from the centre of the valve when such an insert is located therewithin.

The size of the valve 10 and the thickness of the valve leaflets 14, as well as the shape of valve 10, are preferably chosen to provide an optimal balance between: friction between the valve 10 and any insert 16, and sealing strength when the valve 10 is closed. As explained above, the provision of three leaflets 14 is considered the optimal solution.

The valve 10 is preferably of a type intended to be used in an introducer or delivery device used, for example, in delivering stents, stent grafts, vena cava filters, occlusion devices and other implants and prostheses endoluminally into a patient, as well as for devices for effecting endoluminal treatments and diagnosis. Thus, the valve is preferably a haemostatic valve and the element 16 held within the valve can be a pusher, dilator, catheter or any other elongate medical device.

Referring now to FIGS. 3 and 4, there is shown a preferred embodiment of valve 100 to be used as a haemostatic valve in a deployment or delivery device of the type discussed above. In this embodiment, the valve 100 has three elongate leaflets 102 which are connected to one another in sealed manner along their adjacent edges 104.

The leaflets 102 can be sealed to one another after being formed, for example by bonding or welding. In another embodiment, the valve 100 is formed as a unitary structure with the three leaflets and can be manufactured in this form by extrusion, by moulding, such as vacuum or blow moulding, or in any other suitable way. The valve is formed such that it is preferably fluid tight when in use, that is the connections between the leaflets 102 are fluid tight.

Figure 6:
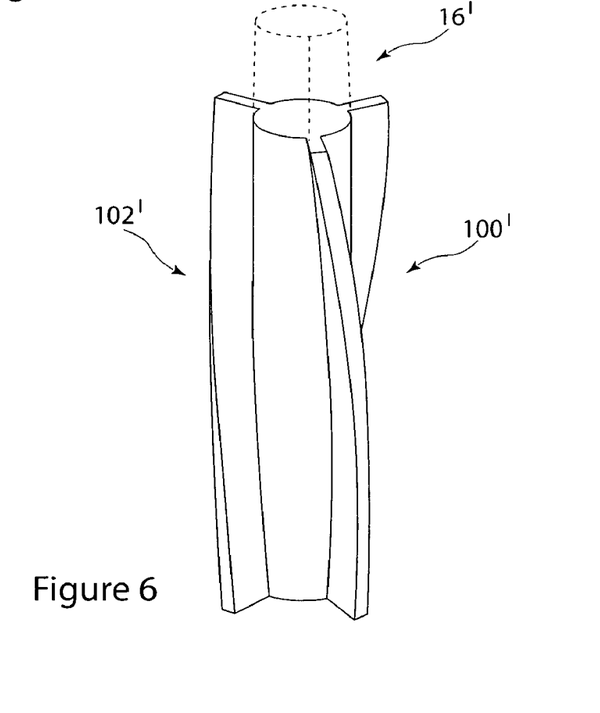
FIG. 6 is a schematic view of a part of the valve element of FIG. 5 closed around an insert.
Figure 7:
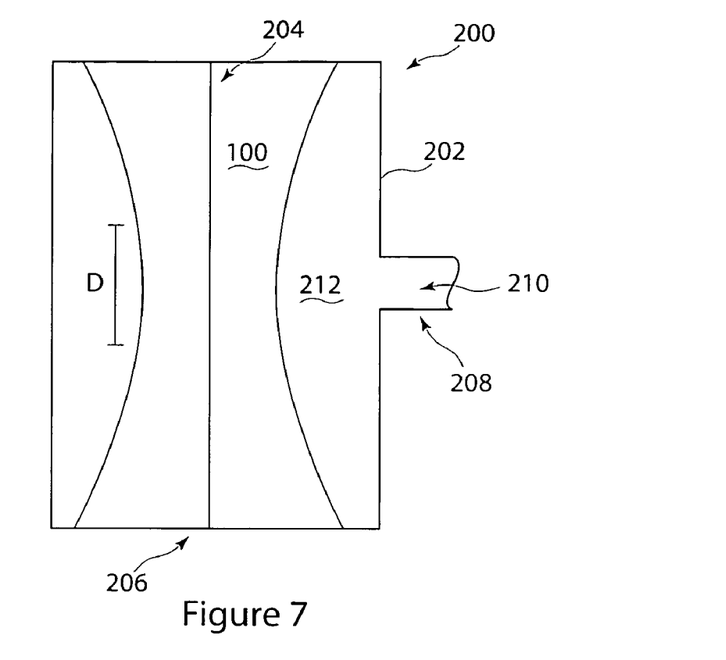
FIG. 7 is a schematic diagram of an embodiment of valve assembly.

As can be seen in FIG. 3, this embodiment of valve 100 has a waist 106, which may be formed as a result of shaping the leaflets of the valve so as to narrow gradually towards their centre points or by stretching the top and bottom edges of the valve 100 radially outwardly and holding these in their stretched conditions by suitable fixing to a valve element housing FIGS. 6 and 7.

In FIG. 3 the waist is shown to be considerably narrower than the ends of the valve 100, although the degree of reduction in the valve diameter from its ends to its centre can be chosen by the skilled person and is dependent upon the application and the sealing characteristics required for the valve 100. For example, in some instances it may be preferable to have a valve which is substantially cylindrical, that is with a very shallow waist 106, whereas in other instances it may be preferable for the valve 100 to have a more pronounced waist 106, for example as shown in FIGS. 3 and 4.

As can be seen in FIG. 4, the waist 106 provides a relatively narrow passage 108 in the middle of the interior of the valve 100, formed by the three leaflets 102. This passage 108 is equivalent to the arrangement shown in FIG. 2 and discussed above.

The valve 100 may typically be made of polyurethane, silicon, rubber, polychloroprene (Neoprene), styrene Butadiene styrene ethylene Butadiene, latex, a rubber like material.

In another embodiment, the valve 100 could be made of a relatively non-compliant material, for example of the type used for dilatation, angioplasty or other balloons of low compliance. Suitable materials include polyethylene terephthalate (PET), polyethylene, nylon, PVC or any other suitable materials known in the art. Such materials can, because of their flexibilities, provide good sealing in such a valve element and exhibit low friction.

As with the embodiment of FIG. 2 the valve 100 could be provided with a hydrophilic coating on its internal surfaces and could also be formed of multi-layered leaflets.

The valve 100 exhibits the advantages discussed above in connection with FIG. 2.

Figure 5:
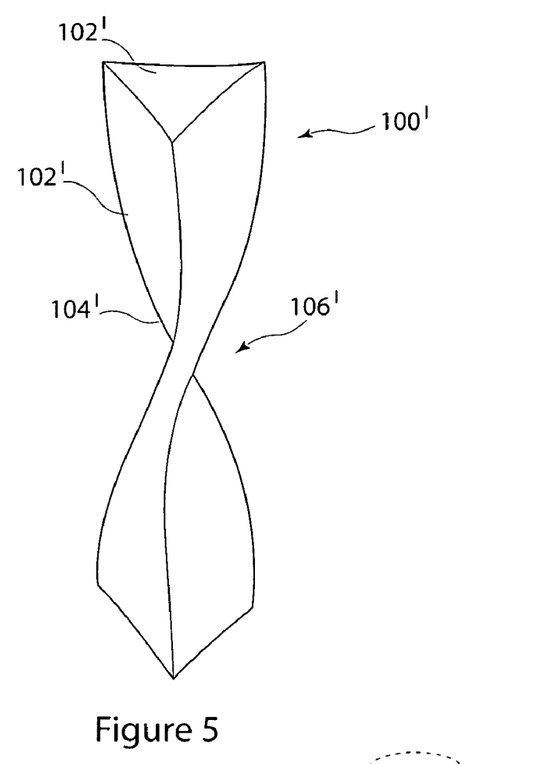
FIG. 5 is a schematic view of an embodiment of valve element which is pre-twisted.

Referring now to FIGS. 5 and 6, there is shown another embodiment of valve element 100'. This valve element 100' has all of the characteristics and alternatives described in connection with the valve elements described above but differs in being pre-twisted. That is, the valve 100' has an unbiased shape which is twisted in its longitudinal direction by, in this embodiment, around 120° from one end of the valve 100' to the other. The amount of twist can be different and the optimum can be determined by trial and error. It is considered that a twist of 60° to 180° is optimal but could be more or less than these. The valve 100' could be twisted in this manner in any of a number of ways, such as by twisting during extrusion or by suitable shaping in a mould.

A pre-twisted shape to the valve 100' facilitates the collapse of the valve leaflets 102' towards the sealed configuration and thus facilitates the formation of a good seal.

FIG. 6 shows an enlarged view of a portion of valve 100' sealed against insert 16'.

The leaflets of this valve and of the other valves disclosed herein could be of a type in which they collapse and/or overlap thus to seal without an insert in the valve.

Turning now to FIG. 7, there is shown an embodiment of valve assembly 200 including therewithin a tri-leaflet valve element 100 of the type shown in FIGS. 3 and 4 or of the type shown in FIGS. 5 and 6. The assembly 200, in this embodiment, includes a casing 202 having openings 204, 206 at either end. The valve 100 is sealed to the casing 202 so that each end of the valve 100 envelops one of the openings 204, 206, so as to provide a channel passing through the centre of the assembly 200, for the passage of an element 16 of the type shown in FIG. 2 and discussed in connection therewith.

Figure 8:
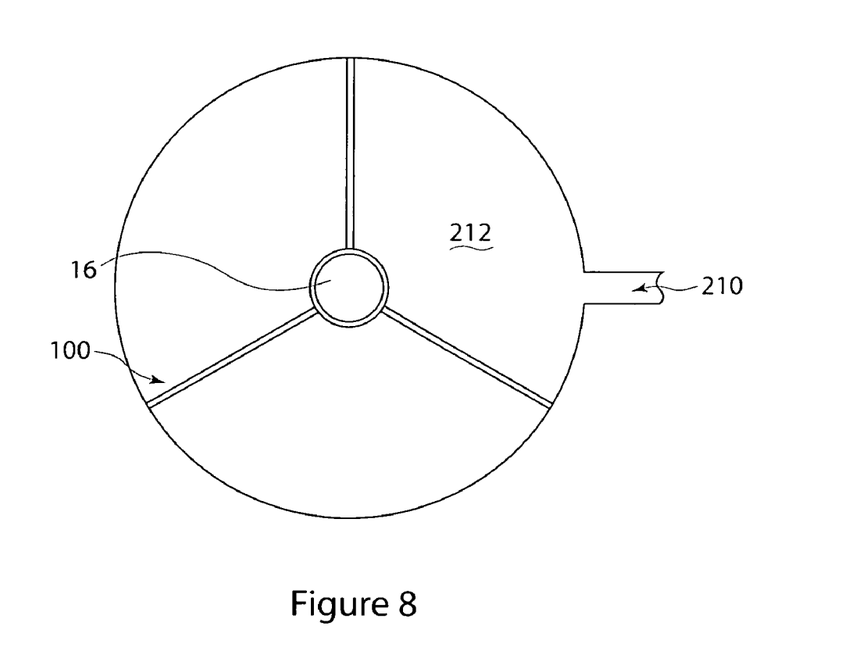
FIG. 8 is a cross-sectional view of the assembly of FIG. 5 showing the valve element at its waist portion in a condition in which it has been pressurized to close.

The casing 202 is provided with a port 208 for the supply of pressured fluid 210 into the chamber 212 which surrounds the outside of the valve element 100. Application of pressurized fluid into the chamber 212 causes the valve leaflets of the valve 100 to be pressed towards the centre of the casing 202 and thereby to constrict the passage between the two openings 204, 206, in other words to compress the central aperture 108 of FIG. 4. This has the effect of closing the valve element 100 into a sealing configuration. When an insert 16 is placed within the valve assembly 200, passing through the openings 204 and 206, pressurization of the chamber 212 causes the leaflets 102 to compress onto the element 16 and to seal either side of that element 16 as will be apparent from the cross-sectional view of FIG. 8. For this purpose, the leaflets 102 are such that they can fold easily onto one another and also onto any insert 16 placed within the valve 100. In this way, a reliable seal can be achieved with the valve 100.

Further details of the valve assembly 200 are disclosed in the applicant's co-pending United States provisional patent application filed on 30 Oct. 2007 and having the No. 61/001,018, as well as the United States patent application being filed claiming priority therefrom.

Figure 9:
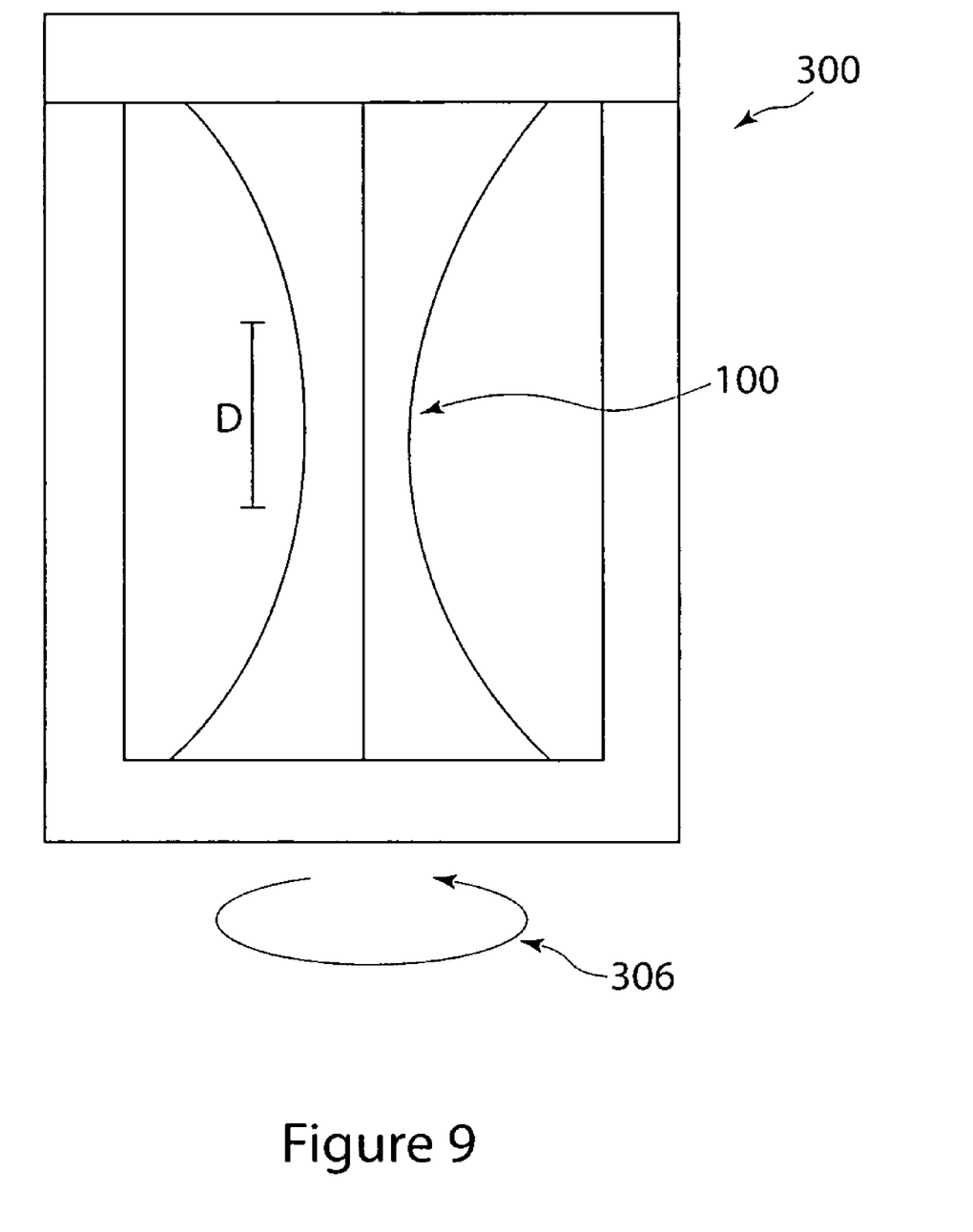
FIG. 9 is a schematic diagram of another embodiment of valve assembly.

FIG. 9 shows in schematic form another embodiment of valve assembly 300 in which the valve 100 is supported by first and second support members 302, 304 which may be part of a casing 310 for the valve 100. Such casing can be any suitable casing which encloses the valve 100, for example one similar to that disclosed in US-2005/0171479 discussed above. The supports 302 and 304 can be rotated relative to one another (typically, one is rotated while the other is stationary), in the direction of the arrow 306, for example. Such rotation causes the valve 100 to twist, with such twisting action causing the leaflets to close the passage 108 therebetween.

As with the embodiment of FIG. 7, the connecting elements 302, 304 have apertures therein (not visible in FIG. 9) such that an element 16, can be inserted into and through the valve 100.

The fact that the valve is formed of a plurality of leaflets 102, as shown in the Figures, in which the leaflets can touch and be very close to the insert 16 held within the valve element, has the effect of causing the leaflets 102 to form a seal of substantial depth, in the example of FIG. 5 or 7 being approximately the length D. Of course, this depth is dependent upon the nature of the waist 106 of the valve 100 and the size of an insert 16 held is within the assembly 300 and passing through the valve 100. It will be appreciated that the depth of the seal produced by a multi-leaflet valve of the type disclosed herein is substantially greater than that provided by prior art valves, such as those disclosed in US-2005/0171479 and US-2004/0178586. This gives a substantially enhanced seal.

It is also envisaged that the valve could be made of polyvinyl acetate (EVA).

The invention claimed is:

1. A haemostatic valve element having first and second ends arranged along a longitudinal axis and a waist portion between the first and second ends, wherein the valve element is formed of at least three elongate flexible leaflets each curving inwardly toward the longitudinal axis and arranged so as to provide a passage therebetween when the valve element is in an open configuration, the leaflets being able to close in on one another along at least a portion thereof, thereby to provide a seal, wherein when the valve element is closed the dimensions of the passage between the leaflets of the valve element in all directions transverse to the longitudinal axis are narrower at the waist portion than at the first and second ends; and wherein longitudinal sides of adjacent leaflets are sealed to one another from the first end of the valve element along the waist portion to the second end of the valve element.

2. A haemostatic valve element according to claim 1, wherein there are provided three leaflets.

3. A haemostatic valve element according to claim 1, wherein the leaflets extend along a major portion of the length of the valve.

4. A haemostatic valve element according to claim 1, wherein the leaflets extend for substantially the entire length of the valve.

5. A haemostatic valve element according to claim 1, wherein the valve element is formed of a compliant material.

6. A haemostatic valve element according to claim 5, wherein the valve element is made of silicon, a rubber or rubber-like material.

7. A haemostatic valve element according to claim 1, wherein the valve element is formed of a non-compliant material.

8. A haemostatic valve element according to claim 7, wherein the valve element is formed from polyethylene terephthalate (PET), polyethylene, nylon or another plastics material.

9. A haemostatic valve element according to claim 1, wherein there is provided a hydrophilic coating on internal surfaces of the valve element within said passage.

10. A haemostatic valve element according to claim 1, wherein the valve element is twisted in a longitudinal direction thereof.

11. A haemostatic valve element according to claim 10, wherein the valve element retains a twisted configuration when unbiased.

12. A haemostatic valve assembly including a valve element according to claim 1 and a valve sealing device for configuring the valve element into a sealed configuration.

13. A haemostatic valve assembly according to claim 12, wherein the valve sealing device includes a pressurizable chamber within which the valve element is located, pressurization of the chamber causing the valve leaflets to close onto one another, thereby to provide a sealing function.

14. A haemostatic valve assembly according to claim 12, wherein the valve sealing device includes a twisting element operable to twist the valve closed thereby to provide a sealing function.

15. A haemostatic valve element formed of at least two leaflets arranged so as to provide a passage therebetween when the valve element is in an open configuration, the leaflets each having an internal surface, the internal surfaces each curving into the passage and being able to close in on one another along at least a portion thereof, thereby to provide a seal; wherein the valve leaflets are formed of a substantially non-compliant material and wherein longitudinal sides of adjacent leaflets are sealed to one another such that a fold is created between the internal surfaces and such that at least a portion of the internal surfaces of adjacent leaflets contact one another in all operating states of the valve.

16. A haemostatic valve element according to claim 15, wherein said valve leaflets are elongate leaflets.

17. A haemostatic valve element according to claim 15, wherein the valve element is formed from polyethylene terephthalate (PET), polyethylene, nylon or another plastics material.

18. An introducer, medical treatment or deployment device including a haemostatic valve element having first and second ends arranged along a longitudinal axis and a waist portion between the first and second ends, wherein the valve element is formed of at least three elongate flexible leaflets each curving inwardly toward the longitudinal axis and arranged so as to provide a passage therebetween when the valve element is in an open configuration, the leaflets being able to close in on one another along at least a portion thereof, thereby to provide a seal, wherein when the valve element is closed the dimensions of the passage between the leaflets of the valve element in all directions transverse to the longitudinal axis are narrower at the waist portion than at the first and second ends; and wherein longitudinal sides of adjacent leaflets are sealed to one another from the first end of the valve element along the waist portion to the second end of the valve element.

* * * * *